US010052632B2

(12) United States Patent
Marble et al.

(10) Patent No.: US 10,052,632 B2
(45) Date of Patent: Aug. 21, 2018

(54) CHANNELS WITH CROSS-SECTIONAL THERMAL GRADIENTS

(71) Applicant: ABBOTT MOLECULAR INC., Des Plaines, IL (US)

(72) Inventors: Herbert A. Marble, Naperville, IL (US); Thomas Laffler, Vista, CA (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 62 days.

(21) Appl. No.: 14/981,158

(22) Filed: Dec. 28, 2015

(65) Prior Publication Data

US 2016/0318023 A1    Nov. 3, 2016

Related U.S. Application Data

(62) Division of application No. 13/724,503, filed on Dec. 21, 2012, now Pat. No. 9,222,115.

(Continued)

(51) Int. Cl.
*C12Q 1/68* (2018.01)
*C12P 19/34* (2006.01)
(Continued)

(52) U.S. Cl.
CPC ........... *B01L 7/54* (2013.01); *B01L 3/502784* (2013.01); *B01L 7/525* (2013.01); *C07H 21/00* (2013.01);
(Continued)

(58) Field of Classification Search
None
See application file for complete search history.

(56) References Cited

U.S. PATENT DOCUMENTS 3,710,933 A    1/1973  Fulwyler et al.
4,230,685 A   10/1980  Senyei et al.
(Continued)

FOREIGN PATENT DOCUMENTS

WO    WO-9722719 A1    6/1997
WO    WO-9740383 A1   10/1997
(Continued)

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.
(Continued)

*Primary Examiner* — Young J Kim
(74) *Attorney, Agent, or Firm* — Casimir Jones, S.C.; David Casimir

(57) ABSTRACT

Provided herein are systems, devices, and methods for generating thermal gradients in channels and uses thereof. In particular, provided herein are system, methods, and devices employing first and second thermal layers positioned around a channel in order to create a thermal gradient across a cross-section of the channel having, for example, a nucleic acid denaturation zone, a nucleic acid annealing zone, and a nucleic acid polymerization zone. Such devices find use in, for example, nucleic acid amplification procedures, including digital polymerase chain reaction (dPCR) to temperature cycle droplets for amplification of nucleic acid templates within the droplets.

17 Claims, 4 Drawing Sheets

Related U.S. Application Data

(60) Provisional application No. 61/582,035, filed on Dec. 30, 2011.

(51) Int. Cl.
   *B01L 7/00* (2006.01)
   *C07H 21/00* (2006.01)
   *B01L 3/00* (2006.01)
   *C12Q 1/686* (2018.01)

(52) U.S. Cl.
   CPC .............. *C12P 19/34* (2013.01); *C12Q 1/686* (2013.01); *B01L 2400/0415* (2013.01); *B01L 2400/0433* (2013.01); *B01L 2400/0445* (2013.01); *B01L 2400/086* (2013.01)

(56) References Cited

U.S. PATENT DOCUMENTS

| | | |
|---|---|---|
| 4,354,114 A | 10/1982 | Karnaukhov et al. |
| 4,361,400 A | 11/1982 | Gray et al. |
| 4,661,225 A | 4/1987 | Penniman et al. |
| 4,710,472 A | 12/1987 | Saur et al. |
| 4,812,394 A | 3/1989 | Dolbeare et al. |
| 4,908,112 A | 3/1990 | Pace |
| 5,104,791 A | 4/1992 | Abbott et al. |
| 5,210,015 A | 5/1993 | Gelfand et al. |
| 5,538,848 A | 7/1996 | Livak et al. |
| 5,605,798 A | 2/1997 | Koester |
| 5,637,469 A | 6/1997 | Wilding et al. |
| 5,695,934 A | 12/1997 | Brenner |
| 5,714,330 A | 2/1998 | Brenner et al. |
| 5,750,341 A | 5/1998 | Macevicz |
| 5,777,324 A | 7/1998 | Hillenkamp |
| 5,863,736 A | 1/1999 | Haaland |
| 5,912,148 A | 6/1999 | Eggerding |
| 5,945,283 A | 8/1999 | Kwok et al. |
| 6,043,031 A | 3/2000 | Koester et al. |
| 6,130,073 A | 10/2000 | Eggerding |
| 6,210,891 B1 | 4/2001 | Nyren et al. |
| 6,258,568 B1 | 7/2001 | Nyren |
| 6,303,343 B1 | 10/2001 | Kopf-Sill |
| 6,306,597 B1 | 10/2001 | Macevicz |
| 6,309,600 B1 | 10/2001 | Hunter |
| 6,337,212 B1 | 1/2002 | Nagle et al. |
| 6,391,559 B1 | 5/2002 | Brown et al. |
| 6,403,338 B1 | 6/2002 | Knapp et al. |
| 6,432,360 B1 | 8/2002 | Church |
| 6,440,722 B1 | 8/2002 | Knapp et al. |
| 6,485,944 B1 | 11/2002 | Church et al. |
| 6,511,803 B1 | 1/2003 | Church et al. |
| 6,524,456 B1 | 2/2003 | Ramsey et al. |
| 6,524,830 B2 | 2/2003 | Kopf-Sill |
| 6,541,274 B2 | 4/2003 | Nagle et al. |
| 6,565,727 B1 | 5/2003 | Shenderov |
| 6,586,176 B1 | 7/2003 | Trnovsky et al. |
| 6,632,655 B1 | 10/2003 | Mehta et al. |
| 6,664,044 B1 | 12/2003 | Sato |
| 6,773,566 B2 | 8/2004 | Shenderov |
| 6,787,308 B2 | 9/2004 | Balasubramanian et al. |
| 6,787,338 B2 | 9/2004 | Wittwer et al. |
| 6,833,246 B2 | 12/2004 | Balasubramanian |
| 6,881,312 B2 | 4/2005 | Kopf-Sill et al. |
| 6,911,132 B2 | 6/2005 | Pamula et al. |
| 6,969,488 B2 | 11/2005 | Bridgham et al. |
| 7,041,481 B2 | 5/2006 | Anderson et al. |
| 7,108,974 B2 | 9/2006 | Ecker et al. |
| 7,115,400 B1 | 10/2006 | Adessi et al. |
| 7,170,050 B2 | 1/2007 | Turner et al. |
| 7,285,411 B1 | 10/2007 | Parce et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,329,492 B2 | 2/2008 | Hardin et al. |
| 7,405,281 B2 | 7/2008 | Xu et al. |
| 7,439,014 B2 | 10/2008 | Pamula et al. |
| 7,440,684 B2 | 10/2008 | Spaid et al. |
| 7,459,315 B2 | 12/2008 | Brown |
| 7,622,076 B2 | 11/2009 | Davies et al. |
| 7,629,124 B2 | 12/2009 | Hasson et al. |
| 7,668,697 B2 | 2/2010 | Volkov et al. |
| 7,709,250 B2 | 5/2010 | Corbett et al. |
| 7,799,553 B2 | 9/2010 | Mathies et al. |
| 7,816,121 B2 | 10/2010 | Pollack et al. |
| 7,824,889 B2 | 11/2010 | Vogelstein et al. |
| 7,833,708 B2 | 11/2010 | Enzelberger et al. |
| 7,842,248 B2 | 11/2010 | McAvoy et al. |
| 7,842,457 B2 | 11/2010 | Berka et al. |
| 7,851,184 B2 | 12/2010 | Pollack et al. |
| 7,888,017 B2 | 2/2011 | Quake et al. |
| 7,901,947 B2 | 3/2011 | Pollack et al. |
| 7,972,778 B2 | 7/2011 | Brown et al. |
| 8,017,322 B2 | 9/2011 | Ecker et al. |
| 8,017,743 B2 | 9/2011 | Ecker et al. |
| 8,041,463 B2 | 10/2011 | Pollack et al. |
| 8,349,276 B2 | 1/2013 | Pamula et al. |
| 2005/0074782 A1 | 4/2005 | Krishnan et al. |
| 2005/0130173 A1 | 6/2005 | Leamon et al. |
| 2006/0153924 A1 | 7/2006 | Griffiths et al. |
| 2006/0254933 A1 | 11/2006 | Adachi et al. |
| 2007/0036511 A1 | 2/2007 | Lundquist et al. |
| 2007/0072196 A1 | 3/2007 | Xu et al. |
| 2007/0077564 A1 | 4/2007 | Roitman et al. |
| 2007/0092914 A1 | 4/2007 | Griffiths et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0172954 A1 | 7/2007 | Ismagilov et al. |
| 2007/0188750 A1 | 8/2007 | Lundquist et al. |
| 2007/0195127 A1 | 8/2007 | Ahn et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0003142 A1 | 1/2008 | Link et al. |
| 2008/0009007 A1 | 1/2008 | Lyle et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0090244 A1 | 4/2008 | Knapp et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2008/0277494 A1 | 11/2008 | Davies et al. |
| 2008/0280331 A1 | 11/2008 | Davies et al. |
| 2009/0035777 A1 | 2/2009 | Kokoris et al. |
| 2009/0286687 A1 | 11/2009 | Dressman et al. |
| 2009/0288710 A1 | 11/2009 | Viovy et al. |
| 2009/0311713 A1 | 12/2009 | Pollack et al. |
| 2009/0325184 A1 | 12/2009 | Woudenberg et al. |
| 2010/0028980 A1 | 2/2010 | Hasson et al. |
| 2010/0035323 A1 | 2/2010 | Ulmer |
| 2010/0092973 A1 | 4/2010 | Davies et al. |
| 2010/0120038 A1 | 5/2010 | Mir et al. |
| 2010/0137163 A1 | 6/2010 | Link et al. |
| 2010/0163412 A1 | 7/2010 | Attinger et al. |

(56) References Cited

U.S. PATENT DOCUMENTS

| | | |
|---|---|---|
| 2010/0167288 A1 | 7/2010 | Gale et al. |
| 2010/0173293 A1 | 7/2010 | Woudenberg et al. |
| 2010/0173394 A1 | 7/2010 | Colston, Jr. et al. |
| 2010/0221713 A1 | 9/2010 | Pollack et al. |
| 2010/0227767 A1 | 9/2010 | Boedicker et al. |
| 2010/0236929 A1 | 9/2010 | Pollack et al. |
| 2010/0248237 A1 | 9/2010 | Froehlich et al. |
| 2010/0285975 A1 | 11/2010 | Mathies et al. |
| 2010/0311599 A1 | 12/2010 | Wheeler et al. |
| 2011/0000560 A1 | 1/2011 | Miller et al. |
| 2011/0048951 A1 | 3/2011 | Wu |
| 2011/0053798 A1 | 3/2011 | Hindson et al. |
| 2011/0092376 A1 | 4/2011 | Colston, Jr. et al. |
| 2011/0100823 A1 | 5/2011 | Pollack et al. |
| 2011/0177563 A1 | 7/2011 | Hahn et al. |
| 2011/0177587 A1 | 7/2011 | Nobile et al. |
| 2011/0201526 A1 | 8/2011 | Berka et al. |
| 2011/0217712 A1 | 9/2011 | Hiddessen et al. |
| 2011/0244455 A1 | 10/2011 | Larson et al. |

FOREIGN PATENT DOCUMENTS

| | | |
|---|---|---|
| WO | WO-0018957 A1 | 4/2000 |
| WO | WO-2006084132 A2 | 8/2006 |

OTHER PUBLICATIONS

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.
Bennett S.T., et al., "Toward the 1,000 Dollars Human Genome," Pharmacogenomics, 2005, vol. 6 (4), pp. 373-382.
Birren B., et al., eds., Genome Analysis—A Laboratory Manual, vol. 1, Cold Spring Harbor Laboratory Press, 1997, Table of Contents.
Brenner S., et al., "Gene Expression Analysis by Massively Parallel Signature Sequencing (MPSS) on Microbead Arrays," Nature Biotechnology, 2000, vol. 18 (6), pp. 630-634.
Burns M.A., et al., "An Integrated Nanoliter DNA Analysis Device," Science, 1998, vol. 282 (5388), pp. 484-487.
Chiou J., et al., "A Closed-Cycle Capillary Polymerase Chain Reaction Machine," Analytical Chemistry, 2001, vol. 73 (9), pp. 2018-2021.
Compton J., "Nucleic Acid Sequence-Based Amplification," Nature, 1991, vol. 350 (6313), pp. 91-92.
Fukuba T., et al., "Microfabricated Flow-through Device for DNA Amplification—Towards in situ Gene Analysis," Chemical Engineering Journal, 2004, vol. 101, pp. 151-156.
Gibson U.E., et al., "A Novel Method for Real Time Quantitative RT-PCR," Genome Research, 1996, vol. 6 (10), pp. 995-1001.
Heid C.A., et al., "Real Time Quantitative PCR," Genome Research, 1996, vol. 6 (10), pp. 986-994.
Holland P.M., et al., "Detection of Specific Polymerase Chain Reaction Product by Utilizing the 5'-3' Exonuclease Activity of Thermus Aquaticus DNA Polymerase," Proceedings of the National Academy of Sciences, 1991, vol. 88 (16), pp. 7276-7280.
International Search Report and Written Opinion for Application No. PCT/US12/71297, dated Mar. 8, 2013, 17 pages.
Kiss M.M., et al., "High-throughput Quantitative Polymerase Chain Reaction in Picoliter Droplets," Analytical Chemistry, 2008, vol. 80 (23), pp. 8975-8981.
Kopp M.U., et al., "Chemical Amplification: Continuous-Flow PCR on a Chip," Science, 1998, vol. 280 (5366), pp. 1046-1048.
Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.
Liu J., et al., "A Nanoliter Rotary Device for Polymerase Chain Reaction," Electrophoresis, 2002, vol. 23 (10), pp. 1531-1536.
Livak K.J., et al., "Oligonucleotides with Fluorescent Dyes at Opposite Ends Provide a Quenched Probe System Useful for Detecting PCR Product and Nucleic Acid Hybridization," PCR Methods and Applications, 1995, vol. 4 (6), pp. 357-362.
Maclean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Mitra R.D., et al., "Fluorescent in Situ Sequencing on Polymerase Colonies," Analytical Biochemistry, 2003, vol. 320 (1), pp. 55-65.
Nakano H., et al., "High Speed Polymerase Chain Reaction in Constant Flow," Bioscience, Biotechnology and Biochemistry, 1994, vol. 58 (2), pp. 349-352.
Nakano M., et al., "Single-Molecule PCR Using Water-in-Oil Emulsion," Journal of Biotechnology, 2003, vol. 102 (2), pp. 117-124.
Neri B.P., et al., "Transferring Automation for Large-scale Development and Production of InvaderTM SNP Assays," In Advances in Nucleic Acid and Protein Analyses, 2000, vol. 3926, pp. 117-125.
Piatek A.S., et al., "Molecular Beacon Sequence Analysis for Detecting Drug Resistance in *Mycobacterium tuberculosis*," Nature Biotechnology, 1998, vol. 16 (4), pp. 359-363.
Shendure J., et al., "Accurate Multiplex Polony Sequencing of an Evolved Bacterial Genome," Science, 2005, vol. 309 (5741), pp. 1728-1732.
Sohn L.L., et al., "Capacitance Cytometry: Measuring Biological Cells One by One," Proceedings of the National Academy of Sciences, 2000, vol. 97 (20), pp. 10687-10690.
Thelwell N., et al., "Mode of Action and Application of Scorpion Primers to Mutation Detection," Nucleic Acids Research, 2000, vol. 28 (19), pp. 3752-3761.
Tyagi S., et al., "Molecular Beacons: Probes that Fluoresce Upon Hybridization," Nature Biotechnology, 1996, vol. 14 (3), pp. 303-308.
Tyagi S., et al., "Multicolor Molecular Beacons for Allele Discrimination," Nature Biotechnology, 1998, vol. 16 (1), pp. 49-53.
Van Dilla M.A., et al., "Flow Cytometry: Instrumentation and Data Analysis, Book Review" Cytometry, 1986, vol. 7, pp. 495.
Voelkerding K.V., et al., "Next-Generation Sequencing: from Basic Research to Diagnostics," Clinical Chemistry, 2009, vol. 55 (4), pp. 641-658.

OPTICAL ARRAY SENSOR

CHANNELS WITH CROSS-SECTIONAL THERMAL GRADIENTS

The present application is a divisional of U.S. application Ser. No. 13/724,503, filed Dec. 21, 2012, which claims priority to U.S. provisional application Ser. No. 61/582,035, filed Dec. 30, 2011, the entirety of each of which is herein incorporated by reference.

FIELD OF THE INVENTION

Provided herein are systems, devices, and methods for generating thermal gradients in channels and uses thereof. In particular, provided herein are systems, methods, and devices employing first and second thermal layers positioned around a channel in order to create a thermal gradient across a cross-section of the channel having, for example, a nucleic acid denaturation zone, a nucleic acid annealing zone, and a nucleic acid polymerization zone. Such devices find use in, for example, nucleic acid amplification procedures, including digital polymerase chain reaction (dPCR) to temperature cycle droplets for amplification of nucleic acid templates within the droplets.

BACKGROUND

The temperature dependence of biochemical and chemical reaction rates poses a particular challenge to efforts to improve reaction efficiency and speed by miniaturization. A time-domain approach, whereby not only the reaction volume but also the entire housing is kept at a desired temperature, is only suitable for isothermal conditions. If temperature needs to be changed or cycled in a rapid and controlled manner, the added thermal mass of the housing limits the rate and/or precision that can be achieved.

In the space-domain approach (see, e.g., Kopp, et al., Science 1998, 280, 1046-1048; Burns, et al., Science 1998, 282, 484-487; Chiou et al., Anal. Chem. 2001, 73, 2018-2021; and Nakano et al., Biosci. Biotechnol. Biochem. 1994, 58, 349-352), different parts of the reaction housing are kept at different temperatures, and reaction volume is brought in thermal contact with a desired part of the housing to keep it at the temperature of that part. If necessary, the reaction volume can then be moved to a different part of the housing to change the temperature; and, depending on the trajectory of the reaction volume, the temperature profile of it can be adjusted or cycled as desired. In the art, most of the implementations of the space-domain dynamic thermal control have been directed to miniaturized PCR thermocycling. Continuous meandering or spiral channels laid across temperature zones have been demonstrated for continuous flow through amplification (see, e.g., Fukuba et al., CHEMICAL ENGINEERING JOURNAL 101 (1-3): 151-156 Aug. 1, 2004); direct-path arrangements with a reaction slug moving back and forth have been described (see, e.g., Chiou et al., Anal. Chem. 2001, 73, 2018-2021); and finally, cycling of an individual reaction through a loop has been demonstrated (see, e.g., Jian Liu Markus Enzelberger et al. Electrophoresis 2002, 23, 1531-1536).

SUMMARY OF THE INVENTION

Provided herein are systems, devices, and methods for generating thermal gradients in channels (e.g., microchannels) and uses thereof. In particular, provided herein are system, methods, and devices employing first and second thermal layers positioned around a channel in order to create a thermal gradient across a cross-section of the channel having, for example, a nucleic acid denaturation zone, a nucleic acid annealing zone, and a nucleic acid polymerization zone. Such devices find use in, for example, nucleic acid amplification procedures, including digital polymerase chain reaction (dPCR) to temperature cycle droplets for amplification of nucleic acid templates within the droplets or other partitions.

In some embodiments, provided herein are devices and systems comprising: a) a channel (e.g., microchannel) comprising a surface configured for transmission of a carrier medium comprising droplets or partitions, b) a first thermal layer positioned along the microchannel configured to heat a portion of the channel surface to a nucleic acid denaturation temperature; and c) a second thermal layer positioned along the channel configured to heat or cool a portion of the channel surface to a nucleic acid annealing temperature; wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone.

In certain embodiments, the devices and systems further comprise a plurality of motion components positioned along the channel (e.g., microchannel), wherein the plurality of motion components are configured to impart motion to the droplets or partitions in the carrier medium when present in the channel such that, for example, random stochastic contact of the droplet or partition with the channel surface is increased. In particular embodiments, motion is imparted via mechanical agitation. In some embodiments, the mechanical agitation is selected from the group consisting of: vibration, low-frequency sonication, and acoustic waves. In some embodiments, the mechanical agitation is imparted with solenoid valves or mechanical switches. In further embodiments, the motion is imparted via convection and/or turbulent flow. In additional embodiments, the motion is imparted via an electrical field. In particular embodiments, the devices and systems further comprise the carrier medium comprising the droplets or partitions. In additional embodiments, the plurality of motion components are positioned intermittently along the channel. In other embodiments, the plurality of motion components are positioned continuously along the channel.

In some embodiments, provided herein are devices and systems comprising: a) a channel (e.g., microchannel) comprising a surface configured for transmission of a carrier medium comprising droplets or partitions, b) a first thermal layer positioned along the microchannel configured to heat a portion of the channel surface to a nucleic acid denaturation temperature; c) a second thermal layer positioned along the channel configured to heat or cool a portion of the channel surface to a nucleic acid annealing temperature; and d) a plurality of motion components positioned along the channel (e.g., microchannel), wherein the plurality of motion components are configured to impart motion (e.g., motion is imparted via mechanical agitation, electrical field, and/or via convection and/or turbulent flow) to the droplets or partitions in the carrier medium when present in the channel such that, for example, random stochastic contact of the droplet or partition with the channel surface is increased (e.g., where the plurality of motion components are positioned intermittently or continuously along the channel); and wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone.

In particular embodiments, provided herein are devices and systems comprising: a) a channel (e.g., microchannel) comprising a surface configured for transmission of a liquid or gas carrier medium (e.g., mineral oil or nitrogen gas) comprising droplets or partitions (e.g., where the droplets or partitions comprise primers, such as amplification primers; and/or comprise dNTPs; and/or comprise a polymerase), b) a first thermal layer positioned along the microchannel configured to heat a portion of the channel surface to a nucleic acid denaturation temperature; and c) a second thermal layer positioned along the channel configured to heat or cool a portion of the channel surface to a nucleic acid annealing temperature; wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone.

In further embodiments, provided herein are devices and systems comprising: a) a channel (e.g., microchannel) comprising a surface configured for transmission of a carrier medium comprising droplets or partitions, b) a first thermal layer positioned along the microchannel configured to heat a portion of the channel surface to a nucleic acid denaturation temperature; c) a second thermal layer positioned along the channel configured to heat or cool a portion of the channel surface to a nucleic acid annealing temperature; and d) optical array sensor positioned along the channel configured to monitor signal output in the droplets or partitions (e.g., the optical array sensor comprises a component selected from the group consisting of: a light-emitting diode, a photodiode array, an optical fiber bundle, a laser configured for fluorometry, a piezoelectric crystal, an interdigital cantilever, a photovoltaic cell, and a gated linear CCD array), wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone.

In particular embodiments, the carrier medium comprises liquid (e.g., mineral oil). In further embodiments, the carrier medium comprises gas (e.g., nitrogen gas). In particular embodiments, the droplets or partitions each comprise primers (e.g., amplification primers) and a nucleic acid template. In other embodiments, the droplets or partitions further comprise a polymerase and dNTPs. In some embodiments, the systems and devices further comprise an optical array sensor positioned along the channel configured to monitor signal output in the droplets or partitions. In certain embodiments, the optical array sensor comprises a component selected from the group consisting of: a light-emitting diode, a photodiode array, an optical fiber bundle, a laser configured for fluorometry, a piezoelectric crystal, an interdigital cantilever, a photovoltaic cell, and a gated linear CCD array.

In certain embodiments, provided herein are devices and systems comprising: a) a channel (e.g., microchannel) comprising a surface configured for transmission of a carrier medium comprising droplets or partitions, b) a first thermal layer positioned along the microchannel configured to heat a portion of the channel surface to a nucleic acid denaturation temperature (e.g., about 90-110 degrees Celsius, such as about 90 . . . 95 . . . 100 . . . 100 . . . 105 . . . or about 110 degrees, or higher); and c) a second thermal layer positioned along the channel configured to heat or cool a portion of the channel surface to a nucleic acid annealing temperature (e.g., about 20-60 degrees Celsius, such as about 20. . . 30 . . . 40 . . . 50 . . . or 60 degrees Celsius); wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone (e.g., which has a temperature of about 60-90 degrees Celsius, such as about 60 . . . 70 . . . 80 . . . or 90 degrees Celsius).

In some embodiments, the denaturation temperature is about 90-110 degrees Celsius (e.g., about 90 . . . 95 . . . 100 . . . 100 . . . 105 . . . or about 110 degrees, or higher). In particular embodiments, the annealing temperature is about 20-60 degrees Celsius (e.g., about 20 . . . 30 . . . 40 . . . 50 . . . or 60 degrees Celsius). In particular embodiments, the nucleic acid polymerization zone has a temperature of about 60-90 degrees Celsius (e.g., 60 . . . 70 . . . 80 . . . or 90 degrees Celsius).

In some embodiments, provided herein are devices and systems comprising: a) a channel (e.g., microchannel) comprising a surface configured for transmission of a carrier medium comprising droplets or partitions (e.g., where the droplets or partitions comprise an emulsion or a macromolecular assembly selected from the group consisting of: unilamellar vesicles, bilamellar vesicles, micelles, liposomes, nanostructures, macromolecular cages, carbon nanotubes, fullerenes or paramagnetic particles), b) a first thermal layer positioned along the microchannel configured to heat a portion of the channel surface to a nucleic acid denaturation temperature; and c) a second thermal layer positioned along the channel configured to heat or cool a portion of the channel surface to a nucleic acid annealing temperature; wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone.

In some embodiments, the droplets or partitions comprise an emulsion or a macromolecular assembly selected from the group consisting of: unilamellar vesicles, bilamellar vesicles, micelles, liposomes, nanostructures, macromolecular cages, carbon nanotubes, and fullerenes.

In certain embodiments, the droplets or partitions comprise paramagnetic microparticles. In further embodiments, the motion component induces an oscillating magnetic field along the channel.

In certain embodiments, provided herein are methods comprising: a) providing a system or device comprising: i) a channel (e.g., microchannel) comprising a surface configured for transmission of a carrier medium comprising droplets or partitions, ii) a first thermal layer positioned along the channel configured to heat a portion of the channel surface to a nucleic acid denaturation temperature; and iii) a second thermal layer positioned along the channel configured to heat or cool a portion of the channel surface to a nucleic acid annealing temperature; wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone; and b) flowing the carrier medium through the channel such that the droplets or partitions repeatedly pass through the thermal gradient causing temperature cycling in the droplets or partitions, wherein the droplets or partitions each comprise primers, a nucleic acid template, a polymerase, nucleotides, salts, and buffer, and wherein the temperature cycling causes amplification of the nucleic acid templates in the droplets or partitions.

In some embodiments, provided herein are methods comprising: a) providing a system or device comprising: i) a channel (e.g., microchannel) comprising a surface configured for transmission of a carrier medium comprising droplets or partitions, ii) a first thermal layer positioned along the channel configured to heat a portion of the channel surface to a nucleic acid denaturation temperature; iii) a second thermal layer positioned along the channel configured to heat or cool a portion of the channel surface to a nucleic acid annealing temperature; and iv) a plurality of motion components positioned along the channel (e.g., microchannel), wherein the plurality of motion components are configured to cause the droplets to repeatedly pass through the thermal gradient by imparting motion to the droplets (e.g., motion is imparted via mechanical agitation, electrical agitation, or convection and/or turbulent flow); wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone; and b) flowing the carrier medium through the channel such that the droplets or partitions repeatedly pass through the thermal gradient causing temperature cycling in the droplets or partitions, wherein the droplets or partitions each comprise primers, a nucleic acid template, a polymerase, nucleotides, salts, and buffer, and wherein the temperature cycling causes amplification of the nucleic acid templates in the droplets or partitions.

In certain embodiments, the device used in the methods further comprises a plurality of motion components positioned along the channel (e.g., microchannel), wherein the plurality of motion components are configured to cause the droplets to repeatedly pass through the thermal gradient by imparting motion to the droplets. In other embodiments, the motion is imparted via mechanical agitation. In other embodiments, the mechanical agitation is selected from the group consisting of: vibration, low-frequency sonication, and acoustic waves. In certain embodiments, the mechanical agitation is imparted with solenoid valves or mechanical switches. In other embodiments, the motion is imparted via convection and/or turbulent flow. In further embodiments, the motion is imparted via an electrical field. In some embodiments, the plurality of motion components are positioned intermittently along the channel.

In certain embodiments, provided herein are methods comprising: a) providing a system or device comprising: i) a channel (e.g., microchannel) comprising a surface configured for transmission of a carrier medium comprising droplets or partitions, ii) a first thermal layer positioned along the channel configured to heat a portion of the channel surface to a nucleic acid denaturation temperature; iii) a second thermal layer positioned along the channel configured to heat or cool a portion of the channel surface to a nucleic acid annealing temperature; and iv) an optical array sensor positioned along the channel (e.g., microchannel); wherein the channel and first and second thermal layers are positioned to create a thermal gradient across a cross-section of the channel, and wherein the thermal gradient comprises a nucleic acid denaturation zone, a nucleic acid annealing zone, and a nucleic acid polymerization zone; b) flowing the carrier medium through the channel such that the droplets or partitions repeatedly pass through the thermal gradient causing temperature cycling in the droplets or partitions, wherein the droplets or partitions each comprise primers, a nucleic acid template, a polymerase, nucleotides, salts, and buffer, and wherein the temperature cycling causes amplification of the nucleic acid templates in the droplets or partitions; and c) monitoring the template amplification with the optical array sensor.

In particular embodiments, the device further comprises an optical array sensor positioned along the channel (e.g., microchannel), and wherein the method further comprises monitoring the template amplification with the optical array sensor. In other embodiments, wherein the optical array sensor comprises a component selected from the group consisting of: a light-emitting diode, a photodiode array, an optical fiber bundle, a laser configured for fluorometry, a piezoelectric crystal, an interdigital cantilever, a photovoltaic cell, and a gated linear CCD array.

In certain embodiments, provided herein are methods comprising: performing digital PCR amplification with droplets, wherein the droplet comprises at least one macromolecular assembly selected from the group consisting of: unilamellar vesicles, bilamellar vesicles,micelles, liposomes, nanostructures, macromolecular cages, carbon nanotubes, and fullerenes. In some embodiments, the methods further comprise sequencing the amplified templates in at least some of the droplets. In some embodiments, flowing the carrier medium through the channel is performed in a continuous manner, a pulsed manner, a batch manner, or fed-batch manner.

In some embodiments, provided herein are methods of analyzing nucleic acid comprising: a) separating a nucleic acid sample into a plurality of partitions, wherein the nucleic acid sample comprises a mixture of nucleic acid molecules and amplification reagents, wherein a portion of the plurality of partitions are single nucleic acid molecule containing partitions, and a portion of the plurality of partitions are zero nucleic acid molecule containing partitions, and the number of partitions containing more than one nucleic acid molecule is zero or a statistically insignificant fraction of the total number of partitions, and wherein the portions comprise at least one macromolecular assembly selected from the group consisting of: unilamellar vesicles, bilamellar vesicles,micelles, liposomes, nanostructures, macromolecular cages, carbon nanotubes, and fullerenes; b) treating the plurality of partitions under amplification conditions such that the single nucleic acid molecule containing partitions become amplicon-containing partitions; and c) physically sorting the plurality of partitions.

DEFINITIONS

Figure 1:
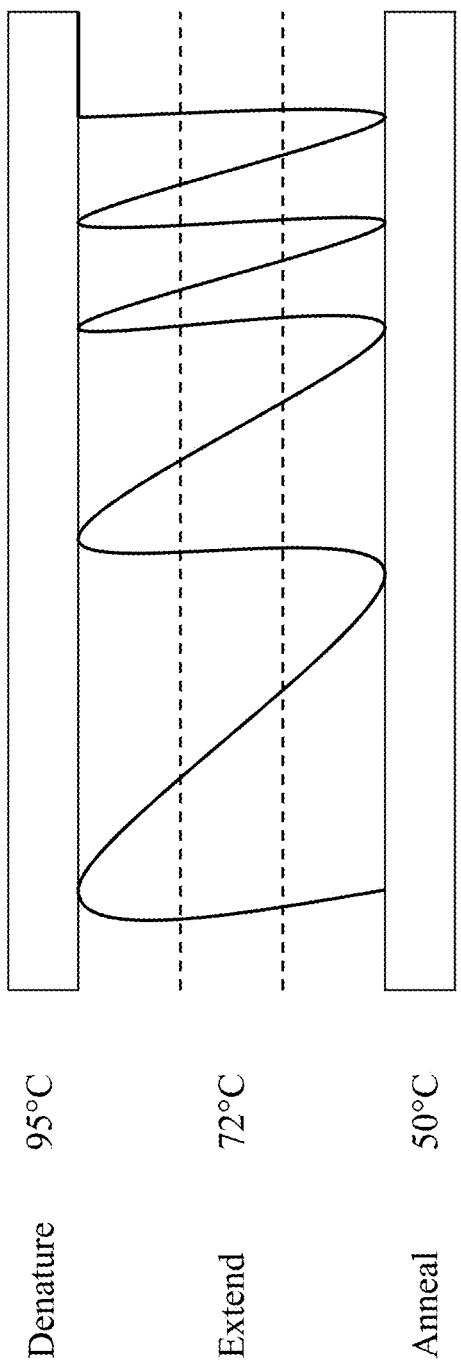
FIG. 1 shows a side view of an exemplary microchannel, with a first thermal layer on 'top' of the microchannel (configured to heat to 95 degrees Celsius) and a second thermal layer on the 'bottom' of the microchannel (configured to heat or cool to 50 degrees Celsius), creating a temperature gradient with a middle zone at 72 degrees Celsius.
Figure 2:
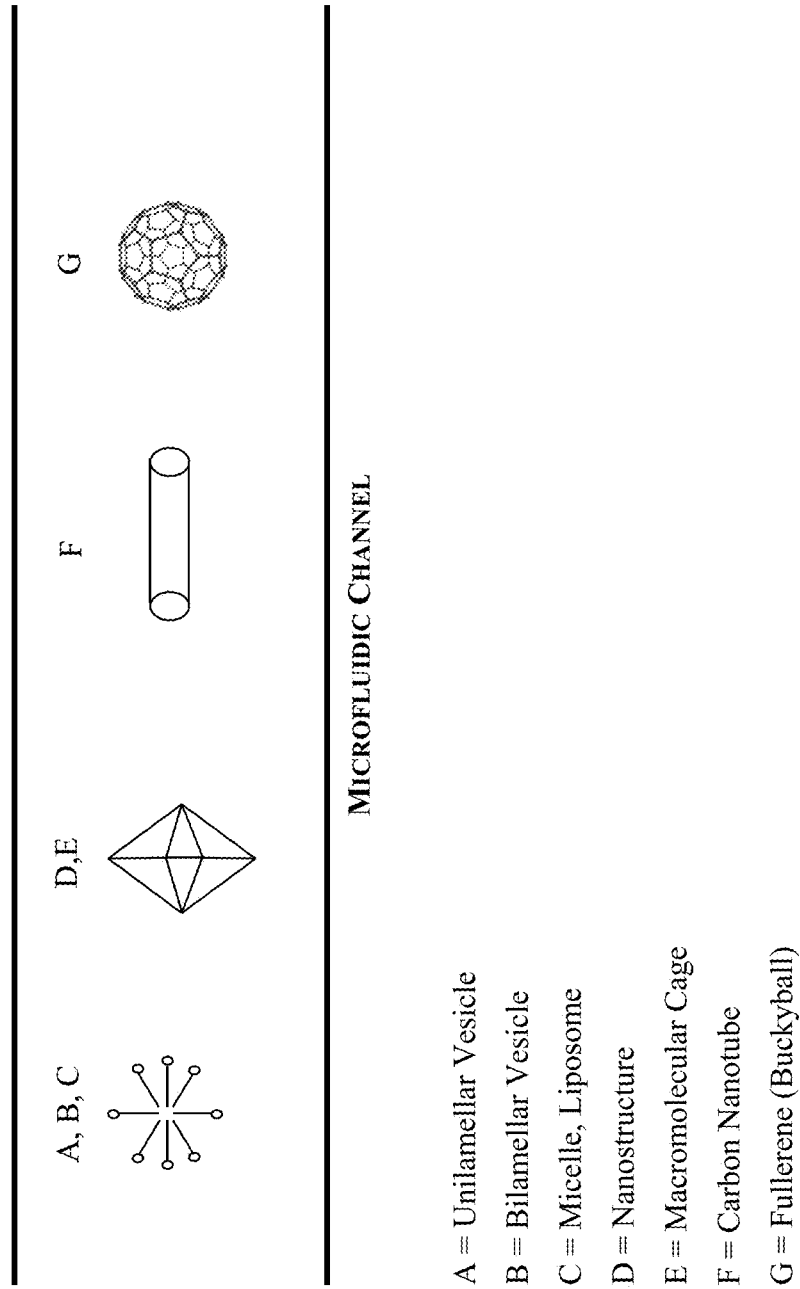
FIG. 2 shows a side view of a microchannel with various macromolecular structures that could be used, for example, with digital PCR amplification methods.
Figure 3:
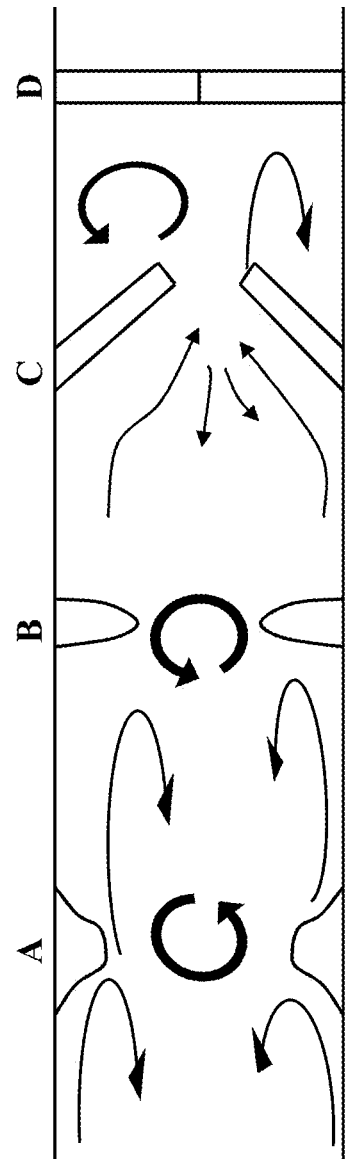
FIG. 3 shows a side view of an exemplary microfluidic channel with various components to create turbulent flow, including barriers, ridges, switches, and valves.
Figure 4:
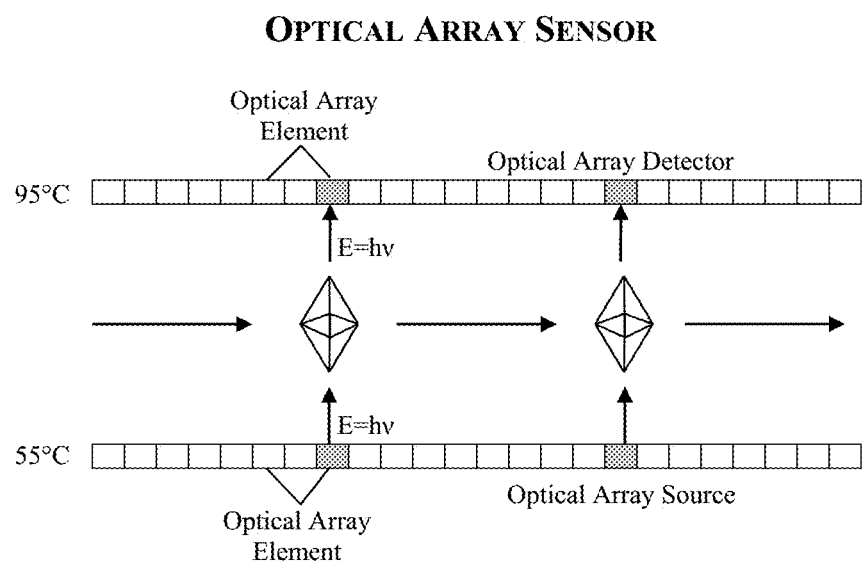
FIG. 4 shows an exemplary optical array sensor along a microchannel.

As used herein, the term "partition" refers to a volume of fluid (e.g. liquid or gas) that is a separated portion of a bulk volume. A bulk volume may be partitioned into any suitable number (e.g. $10^2 \ldots 10^3 \ldots 10^4 \ldots 10^5 \ldots 10^6 \ldots 10^7$, etc.) of smaller volumes (i.e. partitions). Partitions may be separated by a physical barrier or by physical forces (e.g. surface tension, hydrophobic repulsion, etc.). Partitions generated from the larger volume may be substantially uniform in size (monodiperese) or may have non-uniform sizes (polydisperse). Partitions may be produced by any suitable manner (e.g. emulsion, microfluidics, microspray, etc.). Exemplary partitions are droplets.

As used herein, the term "droplet" refers to a small volume of liquid that is immiscible with its surroundings (e.g. gases, liquids, surfaces, etc.). A droplet may reside upon a surface, be encapsulated by a fluid with which it is immiscible (e.g. the continuous phase of an emulsion, a gas (e.g. air, nitrogen)), or a combination thereof. A droplet is typically spherical or substantially spherical in shape, but may be non-spherical. The shape of an otherwise spherical or substantially spherical droplet may be altered by deposition onto a surface. A droplet may be a "simple droplet" or a "compound droplet," wherein one droplet encapsulates one or more additional smaller droplets. The volume of a droplet and/or the average volume of a set of droplets provided herein is typically less than about one microliter (e.g. 1 μL ... 0.1 μL ... 10 nL ... 1 nL ... 100 pL ... 10 pL ... 1 pL ... 100 fL ... 10 fL ... 1 fL). The diameter of a droplet and/or the average diameter of a set of droplets provided herein is typically less than about one millimeter (e.g. 1 mm ... 100 μm ... 10 μm ... 1 μm). Droplets may be formed by any suitable technique (e.g. emulsification, microfluidics, etc.) and may be monodisperse (e.g., substantially monodisperse) or polydisperse.

As used herein, the term "packet" refers to a set of droplets or other isolated partitions disposed in the same continuous volume, in the same region of a continuous volume, on the same surface, or otherwise grouped. A packet may constitute all of the droplets of bulk volume (e.g. an emulsion), or a segregated fraction of droplets from a bulk volume (e.g. at a range of positions along a channel, containing the same target amplicon, etc.). A packet may constitute all the droplets located along a surface (e.g. chip or microfluidic surface), or the droplets in a defined region of a surface. A packet may refer to a set of droplets that when analyzed in partial or total give a statistically relevant sampling for quantitative analysis of the entire starting sample (e.g. the entire bulk volume).

As used herein, the term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable or can be made detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, the term "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, etc.). Samples may be complex samples or mixed samples, which contain nucleic acids comprising multiple different nucleic acid sequences. Samples may comprise nucleic acids from more than one source (e.g. difference species, different subspecies, etc.), subject, and/or individual. In some embodiments, the methods provided herein comprise purifying the sample or purifying the nucleic acid(s) from the sample. In some embodiments, the sample contains purified nucleic acid. In some embodiments, a sample is derived from a biological, clinical, environmental, research, forensic, or other source.

DETAILED DESCRIPTION

Provided herein are systems, devices, and methods for generating thermal gradients in channels (e.g., microchannels) and uses thereof. In particular, provided herein are system, methods, and devices employing first and second thermal layers positioned around a channel in order to create a thermal gradient across a cross-section of the channel having, for example, a nucleic acid denaturation zone, a nucleic acid annealing zone, and a nucleic acid polymerization zone. Such devices find use in, for example, nucleic acid amplification procedures, including digital polymerase chain reaction (dPCR) to temperature cycle droplets for amplification of nucleic acid templates within the droplets or other partitions.

In some embodiments, a sample is analyzed for the presence and/or abundance of target nucleic acid sequences. In some embodiments, the target nucleic acid is present in a potentially complex sample that may contain many different nucleic acid sequences, each of which may or may not contain the target sequence. In some embodiments, a sample is analyzed to determine the proportion of nucleic acid molecules containing a target sequence of interest. In some embodiments, a complex sample is analyzed to detect the presence and/or measure the abundance or relative abundance of multiple target sequences. In some embodiments, methods provided herein are used to determine what sequences are present in a mixed sample and/or in what relative proportions.

Provided herein are channels (e.g., microchannels) with thermal gradients that allow for amplification of templates in droplets. Generally, continuous-flow microfluidic PCR systems require a liquid or gaseous carrier (such as mineral oil or inert gas) to provide bulk fluid or aerosol transport of discrete aqueous phase reaction elements. In certain embodiments, the methods described herein employ oil dispersion or aerosolization to create discrete aqueous phase nanodroplets for transport through microfluidic channels imbedded in a fluid cell device. Droplets containing both DNA targets (amplicons) and amplification reagents (polymerase, dNTPs, buffer, and salt) can be prepared directly in either a biphasic liquid or gaseous carrier stream that is readily dispensed into a microfluidic chamber for subsequent amplification.

In certain embodiments, the methods and devices described herein utilize mechanical agitation to provide intermittent mixing pulses along a microfluidic channel, such that random stochastic contact with surface walls provides sufficient thermal cycling for DNA amplification of sequestered suspensions (e.g., bi-phasic nanodroplets, aerosols, and/or macromolecular assemblies). By controlling microchannel architecture (e.g., path length), virtually any desired sensitivity (e.g., copies per mL) may be attained. In other embodiments, the approach described herein utilizes convection and/or turbulent flow to provide mixing, such that random stochastic contact with surface walls provides sufficient thermal cycling for DNA amplification of sequestered suspensions (e.g., bi-phasic nanodroplets, aerosols, and/or macromolecular assemblies).

In certain embodiments, the methods and devices described herein employ a continuous optical array sensor for monitoring of microfluidic PCR applications. Microfluidic PCR systems (e.g., end-point or real-time) can employ a variety of detection strategies. One approach described herein employs a continuous optical array sensor to monitor signal output along the length of a microfluidic channel.

In certain embodiments, provided herein are methods and devices for rapid, bi-thermal PCR amplification enclosed in a miniaturized fluidic device, providing output for downstream molecular analysis (e.g., flow-cytometry, mass spectrometry, and or microcapillary electrophoresis). In certain embodiments, provided herein are methods for PCR amplification utilizing two distinct isothermal layers (e.g., denaturation zone and annealing zone) to create a temperature gradient across specialized microfluidic channels designed to cycle small-volume fluid elements through the thermal temperature extremes of DNA denaturation (e.g., ~95° C.) and annealing (e.g., ~50° C.). Flow through the bi-thermal microfluidic device may be, for example, continuous or pulsed in order to best optimize/synchronize controlled fluid movement and requisite heat transfer. Bulk fluid displacement may be accomplished using a carrier comprised of liquid (mineral oil) or gas (nitrogen), driven by mechanical pressure (or vacuum). The precise geometric architecture of the microfluidic cell is configured to accommodate amplification of small-size (e.g., 100-500 bp) amplicons that require short primer-extension/elongation times (e.g., polymerization rate of ~300 nucleotides/second) and may be configured to accommodate larger amplicon targets (e.g., 2 Kb or longer).

In certain embodiments, amplification proceeds by conventional means as discrete fluid elements cycle along channels embedded between the opposing isothermal layers, obviating the need for active/dynamic temperature cycling and control. The microfluidic channels are designed to transport the discrete fluid elements through the differential thermal zones in a temporal and spatial manner that sustains the traditional amplification cycle (denaturation, annealing, and extension) and provides uniform and efficient heat transfer for rapid cycling; thereby significantly reducing the overall target amplification time and minimizing the physical system dimensions (footprint). The fluid cell is designed to carry the samples through the three amplification zones in a rapid manner that provides adequate residence times for each of the separate temperature-dependent steps (denaturation, annealing, and catalysis). Sample throughput is limited only by the number of microcapillary channels that are fabricated and interrogated. In certain embodiments, the detection scheme may be, but is not limited to: fluorescence based end-point PCR analysis (e.g., flow cytometry or microcapillary-based detection strategies), label-free end-point PCR (e.g., mass spectrometry), and fluorescence-based Real Time PCR analysis (e.g., utilizing on-board optical detection strategies). Flow cytometry-based detection strategies are best suited for Fluorescence-based end-point PCR analysis, by leveraging the inherent stratification afforded by fluid cell transport. Alternate detection strategies such as microcapillary electrophoresis or conductance-based methods may also be employed. Mass spectrometry is ideally suited for label-free end-point PCR analysis.

In other embodiments, real time PCR applications are employed. Real time detection generally employs a network of optical fluorescence detectors/sensors arrayed around the microcapillary channels in a manner that captures the spatially-distributed, time-resolved fluorescence profile of a discrete amplification reaction.

In certain embodiments, carrier flow through the microfluidic device may be continuous, pulsed, batch, or fed-batch in order to best optimize/synchronize controlled fluid movement and requisite heat transfer for thermal cycling. In order to minimize sample cross-talk between discrete volume entities (containing reactants and separate, discrete amplicons/targets) transported through the amplification chamber, many factors may be controlled including (but not limited to): the size-distribution of the nanodroplets, the concentration of the dispersed nanodroplets in the carrier medium, the flow-rate, and potentially the use of cleaning agents that can be introduced in between serial sample addition steps. Many advantages are conferred by this approach such as: minimizing reagent consumption and costs by reducing amplification reaction volumes to nanoliter or picoliter ranges, expediting heat transfer for rapid thermal cycling, reducing the energy burden for temperature control and heat transfer, increasing sample throughput, and miniaturizing the overall system footprint. Together with the bi-isothermal PCR amplification/detection process described above, this approach provides a strategy for a next-generation, continuous-flow, microfluidic amplification system for end-point and real-time PCR applications, among others.

In certain embodiments, the approach described herein utilizes mechanical agitation (e.g., vibration, low-frequency mild sonication, acoustic waves, solenoid valves, nanomechanical switches, etc.) to provide intermittent mixing pulses along a microfluidic channel, such that random stochastic contact with temperature gradient (e.g., ~50° C. -95° C.) extremes located along the microfluidic channel surface wall provides sufficient thermal cycling for DNA amplification of sequestered suspensions (e.g., bi-phasic nanodroplets, aerosols, and/or macromolecular assemblies encapsulating discrete PCR reactions). Physical channel-length can be manipulated to achieve the desired level of amplification. Since overall amplicon target copy-number in clinical samples are expected to vary over a wide dynamic range, channel lengths can be set to detect different concentrations of target (e.g., as low as 100 targets per mL of blood) by imbedding microfluidic paths of varying length. Carrier flow through the microfluidic PCR device may be, for example, continuous, pulsed, batch, or fed-batch in order to best optimize/synchronize controlled fluid movement and requisite heat transfer for thermal cycling. Many advantages are conferred by this approach, including: minimizing reagent consumption and costs by reducing amplification reaction volumes (e.g., microliter to picoliter range) increasing both assay sensitivity and specificity by signal concentration (e.g., afforded by volume sequestration), expediting heat transfer for rapid thermal cycling, reducing the energy burden for temperature control and heat transfer, increasing sample throughput, and miniaturizing the overall system footprint.

In some embodiments, microencapsulated macromolecular assemblies (including, but not limited to: unilamellar vesicles, bilamellar vesicles, micelles, liposomes, nanostructures, macromolecular cages, carbon nanotubes, and fullerenes) are used as self-contained reaction vessels for use in end-point and/or real time microfluidic PCR applications. Such embodiments employ discrete reaction vessels in a carrier suspension stream. Each microencapsulated vessel contains an amplicons/target in combination with the PCR master-mix required for template amplification. Sequestration of a single polymerase and amplicon DNA target in the presence of primers, deoxynucleotide triphosphates, and fluor-conjugate label should result in both increased assay sensitivity (e.g., due to the volume-localization of the amplified signal) and increased specificity (e.g., as small-volume localization inherently reduces the starting template copy-number). Many advantages are conferred by this approach such as: increased sensitivity, increased specificity, minimizing reagent consumption and costs by reducing amplification reaction volumes to nanoliter or picoliter ranges, expediting heat transfer for rapid thermal cycling, reducing the energy burden for temperature control and heat transfer, increasing sample throughput, and miniaturizing the overall system footprint.

In certain embodiments, by incorporating ridges, barriers, or switches, both convection and turbulent flow can be enhanced to deliver adequate thermal contact with the microfluid channel walls.

In some embodiments, the systems, devices, and methods employ a continuous optical array sensor to monitor PCR signal output along the surface of a microfluidic channel. Optical detection can be accomplished in any number of manners, including, for example: LED (light-emitting diode) photodiode arrays, optical fiber bundles, laser induced fluorometry, piezoelectric crystals, interdigital cantilevers, photovoltaic cells, and gated linear CCD arrays.

The present invention is not limited by the types of samples that are assayed according to the methods disclosed herein and can include, for example, serum, plasma, lymphatic fluid, interstitial fluid, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, gastric fluids, intestinal fluids, saliva, urine, breast milk, and teardrops.

In certain embodiments, the droplets may comprise paramagnetic microparticles (PMPs). In such embodiments, one can employ an oscillating magnetic field to attract droplets containing PMPs to the desired temperature surface. In certain embodiments, the oscillating magnetic field frequency is tuned so that PMP-containing droplets can traverse the thermal regions in a cyclical manner that promotes rapid and efficient PCR amplification. In certain embodiments, the thermal zones are magnetic. However, it is not necessary that the thermal zones, themselves, be magnetic. Rather, in some embodiments, it is practical to apply an external magnetic field to the surroundings. In such a configuration, the PMP-droplets transversely flow through the system (continuous-flow) as they are repeatedly attracted to the desired temperature surface (magnetically driven PCR cycling). In other embodiments, a static "batch" approach is utilized that does not utilize continuous-flow. In some embodiments, it is possible to pause the magnetic field briefly, before oscillation/inversion, so that the PMP-droplets can diffuse towards the intermediate temperature zone for annealing. In general, it follows that the strength and magnitude of the magnetic field is directly proportional to the PMP-droplet migration rate; and that the duration of the magnetic field phase is proportional to thermal "hold" step times. Another advantage of PMP-droplets is that they may be easily manipulated and collected downstream using magnetic fields.

In some embodiments, one can use a macromolecular cage to partition and confine reaction elements. Macromolecular cages may also be derivatized with paramagnetic materials that impart a response in a magnetic field.

In certain embodiments, droplet migration is driven electronically by using an electrical field to draw the drops towards a thermal layer. In further embodiments, macromolecular cages are derivatized with charged functional groups to promote desired migration in the electric field.

In some embodiments, all or a portion of the nucleic acid to be analyzed or manipulated is partitioned, for example, from different nucleic acid molecules or from other copies of the same nucleic acid molecule. Nucleic acid molecules may be segregated into droplets and/or may be associated with solid surfaces (e.g., beads) that are themselves segregated from one another. In some embodiments, provided herein is amplification (e.g. PCR amplification) of the partitioned nucleic acids of a sample. In some embodiments, amplification reagents (e.g. primers) are added to a sample prior to partitioning and/or concurrent with partitioning, or amplification reagents are added to the partitioned sample. In some embodiments, primers are hybridized to template nucleic acids prior to partitioning. In some embodiments, all partitions are subjected to amplification conditions (e.g. reagents and thermal cycling), but amplification only occurs in partitions containing target nucleic acids (e.g. nucleic acids containing sequences complimentary to primers added to the sample). In some embodiments, amplification of nucleic acids in partitioned samples results in some partitions containing multiple copies of target nucleic acids and other partitions containing no nucleic acids and/or no target nucleic acids (e.g. containing one non-target nucleic acid molecule).

In some embodiments, detection reagents (e.g., fluorescent labels or other optical or non-optical labels) are included with amplification reagents added to the bulk or partitioned sample. In some embodiments, amplification reagents also serve as detection reagents. In some embodiments, detection reagents are added to partitions following amplification. In some embodiments, detection reagents comprise fluorescent labels. In some embodiments, amplified target nucleic acids (amplicons) are detectable via detection reagents in their partition. In some embodiments, unamplified and/or non-target nucleic acid molecules are not detected. In some embodiments, partitions containing amplified nucleic acids are detectable using one or more detection reagents (e.g. fluorescent labels). In some embodiments, for example where digital approaches are employed, partitions that do not contain amplified nucleic acid, contain unamplified nucleic acid, and/or contain no nucleic acid are either detectable as such, or are undetectable. In some embodiments, measurements of the relative proportion of target nucleic acids in a sample (e.g. relative to other targets nucleic acids, relative to non-target nucleic acids, relative to total nucleic acids, etc.) or the concentration of target nucleic acids in a sample can be measured based on the detection of partitions containing amplified target sequences.

In some embodiments, following amplification, partitions containing amplified target nucleic acids (amplicons) are sorted from partitions not containing amplicons, from partitions not containing nucleic acids, or from amplicons containing other amplified targets. In some embodiments, partitions are sorted based on physical, chemical, and/or optical characteristics of the partition, the nucleic acids therein (e.g. concentration), and/or labels therein (e.g. fluorescent labels). In some embodiments, individual partitions are isolated for subsequent manipulation, processing, and/or analysis of the amplicons therein. In some embodiments, partitions containing similar characteristics (e.g. same fluorescent labels, similar nucleic acid concentrations, etc.) are grouped (e.g. into packets) for subsequent manipulation, processing, and/or analysis (e.g. of the partitions or of the amplicons therein, etc.).

In some embodiments, amplified and/or sorted nucleic acids are re-amplified to increase amplicon concentration within a partition for subsequent manipulation, processing, and/or analysis. In some embodiments, amplified and/or sorted nucleic acids are re-amplified to incorporate sequencing reagents into amplicons. In some embodiments, amplified, sorted, and/or re-amplified target nucleic acid molecules are sequenced according to sequencing methods understood in the art. In some embodiment, amplicons are analyzed using compositions and methods understood in the art (e.g. sequencing, mass spectrometry, spectroscopy, hybridization, etc.).

I. Partitioning

In some embodiments, provided herein are systems, devices, and methods for dividing volumes of fluid and/or reagents into partitions (e.g. droplets). In some embodiments, the systems, devices, and methods utilizes partitioning systems, devices, and/or methods. In some embodiments, exemplary partitioning methods and systems include one or more of emulsification, droplet actuation, microfluidics platforms, continuous-flow microfluidics, reagent immobilization, and combinations thereof.

In some embodiments, the systems, methods, and devices described herein find use for digital PCR, other digital amplification reactions, droplet-based PCR, or other amplification or nucleic acid manipulation reactions employing partitioned, segregated, or transported samples (see e.g., U.S. Pat. Nos., 7,041,481, 7,323,305, 7,842,457, 7,323,305, 6,303,343, 7,459,315, 7,888,017, 7,824,889, 7,629,124, 6,586,176, 6,664,044, 6,524,456, and 6,309,600, and U.S. Pat. Publ. Nos. 20110201526, 20090286687, 20100173293, 20090325184, 20100221713, 20080090244, 20100120038, 20110092376, 20110217712, 20110053798, 20110244455, 20100248237, 20100092973, 20070195127, 20060153924, 20070092914, 20090311713, 20100035323, and 20100227767, herein incorporated by reference in their entireties). In some embodiments, the systems, methods, and devices described herein may be integrated into, integrate, or modify existing systems, devices, and methods (see e.g., U.S. Pat. Nos., 6,337,212, 6,541,274, 7,440,684, 6,524,830, 7,799,553, 6,787,338, 7,901,947, 7,439,014, 8,041,463, 7,816,121, 7,851,184, 7,709,250, 7,972,778, 7,833,708, 7,285,411, 6,440,722, 6,403,338, 6,632,655, 6,881,312, 6,391,559, and 7,622,076, and U.S. Pat. Publ. Nos. 20110177563, 20110177587, 20110048951, 20080280331, 20070172954, 20110000560, 20080003142, 20100137163, 20100285975, 20080277494, and 20100028980, herein incorporated by reference in their entireties).

In some embodiments, partitioning is performed to divide a sample into a sufficient number of partitions such that each partition contains one or zero nucleic acid molecules. In some embodiments, partitions are produced at small enough size such that each partition contains one or zero nucleic acid molecules. In some embodiments, the number and size of partitions is based on the concentration and volume of the bulk sample. In some embodiments, the number of nucleic acid molecules to be partitioned is low, relative to the number of partitions. In some embodiments, based on the relatively low number of target nucleic acid molecules compared to partitions, the likelihood of a partition containing 2 or more target nucleic acid molecules is low (e.g. 0.1% . . . 0.01% . . . 0.001% . . . 0.0001% . . . 0.00001% . . . 0.000001). In some embodiments, the number of partitions containing 2 or more nucleic acid molecules is zero. In some embodiments, the number of partitions containing 2 or more nucleic acid molecules is essentially zero, or a statistically insignificant fraction of the totally number of partitions.

In some embodiments, provided herein are systems, methods, and devices for partitioning a bulk volume into partitions (e.g. droplets) by emulsification (Nakano et al. J Biotechnol 2003; 102:117-124.; Margulies et al. Nature 2005; 437:376-380.; herein incorporated by reference in their entireties). In some embodiments, provided herein are systems and methods for generating "water-in-oil" droplets (U.S. Pat. App. No. 20100173394; herein incorporated by reference in its entirety).

In some embodiments, provided herein are microfluidics systems, methods, and devices for partitioning a bulk volume into partitions (U.S. Pat. App. No. 20100236929; U.S. Pat. App. No. 20100311599; U.S. Pat. App. No. 20100163412; U.S. Pat. No. 7,851,184; herein incorporated by reference in their entireties). In some embodiments, microfluidic systems are configured to generate monodisperse droplets (Kiss et al. Anal Chem. 2008 Dec. 1; 80(23): 8975-8981; herein incorporated by reference in its entirety). In some embodiments, provided herein are microfluidics systems for manipulating and/or partitioning samples. In some embodiments, a microfluidics system comprises one or more of channels, valves, pumps, etc. (U.S. Pat. No. 7,842, 248, herein incorporated by reference in its entirety). In some embodiments, a microfluidics system is a continuous-flow microfluidics system (Kopp et al., Science, vol. 280, pp. 1046-1048, 1998.; herein incorporated by reference in its entirety). In some embodiments, microarchitecture includes, but is not limited to microchannels, microfluidic plates, fixed microchannels, networks of microchannels, internal pumps; external pumps, valves, centrifugal force elements, etc. In some embodiments, the microarchitecture of the (e.g. droplet microactuator, microfluidics platform, and/or continuous-flow microfluidics) is complemented or supplemented with droplet manipulation techniques, including, but not limited to electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components) and such combination approaches involving discrete droplet operations and microfluidics elements are within the scope of the invention.

In some embodiments, provided herein is a droplet microactuator. In some embodiments, a droplet microactuator is capable of effecting droplet manipulation and/or operations, such as dispensing, splitting, transporting, merging, mixing, agitating, and the like. In some embodiments the invention employs droplet operation structures and techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; U.S. Patent Publication No. 20060254933, entitled "Device for transporting liquid and system for analyzing" published on Nov. 16, 2006 by Adachi et al., the disclosures of which are incorporated herein by reference in their entireties. Droplet manipulation is, in some embodiments, accomplished using electric field mediated actuation. In such embodiments, electrodes are electronically coupled to a means for controlling electrical connections to the droplet microactuator. An exemplary droplet microactuator includes a substrate including a path and/or array of electrodes. In some embodiments, a droplet microactuator includes two parallel substrates separated by a gap and an array of electrodes on one or both substrates. One or both of the substrates may be a plate.

II. Amplification

In some embodiments, provided herein are compositions and methods for the amplification of nucleic acids (e.g. DNA, RNA, etc.). In some embodiments, amplification is performed on a bulk sample of nucleic acids. In some embodiments, amplification is performed on a sample that has been divided into partitions (e.g. droplets). In some embodiments, an amplification reaction is carried out within each partition. In some embodiments, a partition contains all the reagents necessary for nucleic acid amplification. In some embodiments, amplification is performed on a single nucleic acid target molecule within a partition. In some embodiments, template nucleic acid is the limiting reagent in a partitioned amplification reaction. In some embodiments, a partition contains one or zero target (e.g. template) nucleic acid molecules.

In some embodiments, provided herein are compositions (e.g. primers, buffers, salts, nucleic acid targets, etc.) and methods for the amplification of nucleic acid (e.g. digital droplet amplification, PCR amplification, partitioned amplification, combinations thereof, etc.). In some embodiments, an amplification reaction is any reaction in which nucleic acid replication occurs repeatedly over time to form multiple copies of at least one segment of a template or target nucleic acid molecule (e.g. DNA, RNA). In some embodiments, amplification generates an exponential or linear increase in the number of copies of the template nucleic acid. Amplifications may produce in excess of a 1,000-fold increase in template copy-number and/or target-detection signal. Exemplary amplification reactions include, but are not limited to the polymerase chain reaction (PCR) or ligase chain reaction (LCR), each of which is driven by thermal cycling.

Amplification may be performed with any suitable reagents (e.g. template nucleic acid (e.g. DNA or RNA), primers, probes, buffers, replication catalyzing enzyme (e.g. DNA polymerase, RNA polymerase), nucleotides, salts (e.g. $MgCl_2$), etc. In some embodiments, an amplification mixture includes any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), etc.

In some embodiments, the systems, devices, and methods utilize nucleic acid amplification that relies on alternating cycles of heating and cooling (i.e., thermal cycling) to achieve successive rounds of replication (e.g., PCR). In some embodiments, PCR is used to amplify target nucleic acids (e.g. partitioned targets). PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. Typical PCR methods produce an exponential increase in the amount of a product amplicon over successive cycles, although linear PCR methods also find use.

Any suitable PCR methodology, combination of PCR methodologies, or combination of amplification techniques may be utilized, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, etc.

In some embodiments, provided herein are digital PCR methods. In some embodiments, PCR is performed on portions of a sample (e.g. partitions) to determine the presence or absence, concentration, and/or copy number of a nucleic acid target in the sample, based on how many of the sample portions support amplification of the target. In some embodiments, PCR is performed on portions of a sample (e.g. partitions) to detect more than one target nucleic acid and/or to determine the concentration, and/or relative concentrations of multiple target nucleic acids within a sample. In some embodiments, digital PCR is performed as endpoint PCR (e.g., for each of the partitions). In some embodiments, digital PCR is performed as real-time PCR (e.g., for each of the partitions).

PCR theoretically results in an exponential amplification of a nucleic acid sequence (e.g. template or target nucleic acid) from a sample. By measuring the number of amplification cycles required to achieve a threshold level of amplification (as in real-time PCR), the starting concentration of nucleic acid can be calculated. However, there are many factors the affect the exponential amplification of the PCR process, such as varying amplification efficiencies, presence of PCR inhibitors, low copy numbers of starting nucleic acid, and competition with background contaminant nucleic acid. Digital PCR is generally insensitive to these factors, since it does not rely on the assumption that the PCR process is exponential. In digital PCR, individual nucleic acid molecules are separated from the initial sample into partitions, and then amplified to detectable levels. Each partition then provides digital information on the presence or absence of each individual nucleic acid molecule within each partition. When enough partitions are measured using this technique, the digital information can be consolidated to make a statistically relevant measure of starting concentration for the nucleic acid target in the sample. In embodiments in which multiple target nucleic acids are analyzed, digital PCR provides statistically relevant measure of the relative concentrations or ratios to multiple target nucleic acids.

In some embodiments, provided herein is qualitative PCR. In some embodiments, qualitative PCR-based analysis determines whether or not a target is present in a sample (e.g. whether or not a target is present in a partition), generally without any substantial quantification of target. In some embodiments, digital PCR that is qualitative may be performed by determining whether a partition or droplet is positive for the presence of target. In some embodiments, qualitative digital PCR is used to determine the percentage of partitions in a packet that are positive for the presence of target. In some embodiments, qualitative digital PCR is used to determine whether a packet of droplets contains at least a threshold percentage of positive droplets (i.e. a positive sample). In some embodiments, qualitative PCR is performed to detect the presence of multiple targets in a sample.

In some embodiments, the systems, devices, and methods employ RT-PCR (reverse transcription-PCR). In some embodiments, the systems, devices, and methods employ real-time PCR. In some embodiments, the systems, devices, and methods employ endpoint PCR.

III. Amplicon detection

In some embodiments, provided herein are systems, devices, methods, and compositions to identify the presence of nucleic acids (e.g. amplicons, labeled nucleic acids). In some embodiments, detection involves measurement or detection of a characteristic of an amplified nucleic acid, a component (e.g., droplet or partition) comprising amplified nucleic acid, or a byproduct of the amplification process, such as a physical, chemical, luminescence, or electrical aspect, which correlates with amplification (e.g. fluorescence, pH change, heat change, etc.).

In some embodiments, fluorescence detection methods are provided for detection of amplified nucleic acid, and/or identification of partitions containing amplified nucleic acids. In addition to the reagents already discussed, and those known to those of skill in the art of nucleic acid amplification and detection, various detection reagents, such as fluorescent and non-fluorescent dyes and probes are provided. For example, the protocols may employ reagents suitable for use in a TaqMan reaction, such as a TaqMan probe; reagents suitable for use in a SYBR Green fluorescence detection; reagents suitable for use in a molecular beacon reaction, such as molecular beacon probes; reagents suitable for use in a scorpion reaction, such as a scorpion probe; reagents suitable for use in a fluorescent DNA-binding dye-type reaction, such as a fluorescent probe; and/or reagents for use in a LightUp protocol, such as a LightUp probe. In some embodiments, provided herein are methods and compositions for detecting and/or quantifying a detectable signal (e.g. fluorescence) from partitions containing amplified target nucleic acid. Thus, for example, methods may employ labeling (e.g. during amplification, post-amplification) amplified nucleic acids with a detectable label, exposing partitions to a light source at a wavelength selected to cause the detectable label to fluoresce, and detecting and/or measuring the resulting fluorescence. Fluorescence emitted from the partitions can be tracked during amplification reaction to permit monitoring of the reaction (e.g., using a SYBR Green-type compound), or fluorescence can be measure post-amplification.

In some embodiments, detection of amplified nucleic acids employs one or more of fluorescent labeling, fluorescent intercalation dyes, FRET-based detection methods (U.S. Pat. No. 5,945,283; PCT Publication WO 97/22719; both of which are incorporated by reference in their entireties), quantitative PCR, real-time fluorogenic methods (U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety), molecular beacons (Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998); herein incorporated by reference in their entireties), Invader assays (Third Wave Technologies, (Madison, Wis.)) (Neri, B. P., et al., Advances in Nucleic Acid and Protein Analysis 3826:117-125, 2000; herein incorporated by reference in its entirety), nucleic acid sequence-based amplification (NASBA; (See, e.g., Compton, J. Nucleic Acid Sequence-based Amplification, Nature 350: 91-91, 1991.; herein incorporated by reference in its entirety), Scorpion probes (Thelwell, et al. Nucleic Acids Research, 28:3752-3761, 2000; herein incorporated by reference in its entirety), capacitive DNA detection (See, e.g., Sohn, et al. (2000) Proc. Natl. Acad. Sci. U.S.A. 97:10687-10690; herein incorporated by reference in its entirety), etc.

IV. Amplicon Isolation

In some embodiments, provided herein are methods for sorting and/or isolation of amplified nucleic acid. In some embodiments, provided herein are methods to sort and/or isolate partitions containing amplified nucleic acid. In some embodiments, following amplification of target sequences and/or detection of amplicons, partitions containing amplicons are sorted for subsequent manipulation (e.g. re-amplification, labeling, restriction digestion, etc.) and/or analysis (e.g. sequencing, mass detection, etc.).

In some embodiments, amplicons are labeled with detectable and/or manipulatable labels (e.g. fluorescent dyes), during or after amplification, by accepted methods understood to those in the art (e.g., intercalation, incorporation, hybridization, etc.) In some embodiments, partitions containing labeled amplicons are detected and/or sorted (e.g. segregated from non-amplicon-containing partitions, grouped according to presence of a particular label, etc.). For example, in some embodiments, amplicon-containing partitions are mechanically separated by micro-manipulators, electrophoresis, flow cytometry, or other sorting techniques known to those in the art. The following references provide guidance for selecting means for analyzing and/or sorting microparticles: Pace, U.S. Pat. No. 4,908,112; Saur et al., U.S. Pat. No. 4,710,472; Senyei et al., U.S. Pat. No. 4,230,685; Wilding et al., U.S. Pat. No. 5,637,469; Penniman et al., U.S. Pat. No. 4,661,225; Kamaukhov et al., U.S. Pat. No. 4,354,114; Abbott et al., U.S. Pat. No. 5,104,791; Gavin et al., PCT publication WO 97/40383; herein incorporated by reference in their entireties.

In some embodiments, partitions containing fluorescently labeled DNA strands are detected, classified, isolated, and/or sorted by fluorescence-activated cell sorting (FACS; See, e.g., Van Dilla et al., Flow Cytometry: Instrumentation and Data Analysis (Academic Press, New York, 1985); Fulwyler et al., U.S. Pat. No. 3,710,933; Gray et al., U.S. Pat. No. 4,361,400; Dolbeare et al., U.S. Pat. No. 4,812,394; herein incorporated by reference in their entireties. In some embodiments, amplicons are fluorescently labeled with detectable and/or manipulatable fluorescent labels, during or after amplification, by accepted methods understood to those in the art (e.g., intercalation, incorporation, hybridization, etc.). In some embodiments, upon excitation with one or more high intensity light sources, such as a laser, a mercury arc lamp, or the like, each partition containing amplified (and labeled) target nucleic acids will generate fluorescent signals. In some embodiments, partitions exhibiting fluorescence above background, or above a threshold level, are sorted by a FACS instrument, according to methods understood by those of skill in the art. Thus, in some embodiments, partitions are sorted according to their relative optical signal, and collected for further analysis by accumulating those partitions generating a signal within a predetermined range of values corresponding to the presence of amplified target nucleic acid. In some embodiments, partitions are sorted and transferred to reaction vessels and/or platforms suitable for subsequent manipulation, processing, and/or analysis.

V. Analysis

Amplified nucleic acid molecules may be analyzed by any number of techniques to determine the presence of, amount of, or identity of the molecule. Non-limiting examples include sequencing, mass determination, and base composition determination. The analysis may identify the sequence of all or a part of the amplified nucleic acid or one or more of its properties or characteristics to reveal the desired information. For example, in some embodiments, the presence of a polymorphism is determined, for example, to provide information about the nature of an organism (e.g., pathogen), a disease state, a metabolic state, and the like. In some embodiments, the methylation status of a nucleic acid is determined. In some such embodiments, a target nucleic acid may be chemically modified (e.g., via bisulfate treatment) prior to amplification to create a marker for the methylation sites.

Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, and 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; and 5,714,330; herein incorporated by reference in their entireties) and the Adessi PCR colony technology (Adessi et al. (2000). Nucleic Acid Res. 28, E87; WO 00018957; herein incorporated by reference in its entirety).

In some embodiments, chain terminator sequencing is utilized. Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotiter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

Another exemplary nucleic acid sequencing approach that may be adapted for use with the systems, devices, and methods was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Patent Publication No. 20090035777, entitled "HIGH THROUGHPUT NUCLEIC ACID SEQUENCING BY EXPANSION," that was filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-658, 2009; and 7,329,492; U.S. patent application Ser. No. 11/671956; U.S. patent application Ser. No. 11/781166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al., U.S. Pat. No. 7,315,019, entitled "Arrays of optical confinements and uses thereof", issued Jan. 1, 2008 to Turner et al., U.S. Pat. No. 7,313,308, entitled "Optical analysis of molecules", issued Dec. 25, 2007 to Turner et al., U.S. Pat. No. 7,302,146, entitled "Apparatus and method for analysis of molecules", issued Nov. 27, 2007 to Turner et al., and U.S. Pat. No. 7,170,050, entitled "Apparatus and methods for optical analysis of molecules", issued Jan. 30, 2007 to Turner et al., U.S. Patent Publications Nos. 20080212960, entitled "Methods and systems for simultaneous real-time monitoring of optical signals from multiple sources", filed Oct. 26, 2007 by Lundquist et al., 20080206764, entitled "Flowcell system for single molecule detection", filed Oct. 26, 2007 by Williams et al., 20080199932, entitled "Active surface coupled polymerases", filed Oct. 26, 2007 by Hanzel et al., 20080199874, entitled "CONTROLLABLE STRAND SCISSION OF MINI CIRCLE DNA", filed Feb. 11, 2008 by Otto et al., 20080176769, entitled "Articles having localized molecules disposed thereon and methods of producing same", filed Oct. 26, 2007 by Rank et al., 20080176316, entitled "Mitigation of photodamage in analytical reactions", filed Oct. 31, 2007 by Eid et al., 20080176241, entitled "Mitigation of photodamage in analytical reactions", filed Oct. 31, 2007 by Eid et al., 20080165346, entitled "Methods and systems for simultaneous real-time monitoring of optical signals from multiple sources", filed Oct. 26, 2007 by Lundquist et al., 20080160531, entitled "Uniform surfaces for hybrid material substrates and methods for making and using same", filed Oct. 31, 2007 by Korlach, 20080157005, entitled "Methods and systems for simultaneous real-time monitoring of optical signals from multiple sources", filed Oct. 26, 2007 by Lundquist et al., 20080153100, entitled "Articles having localized molecules disposed thereon and methods of producing same", filed Oct. 31, 2007 by Rank et al., 20080153095, entitled "CHARGE SWITCH NUCLEOTIDES", filed Oct. 26, 2007 by Williams et al., 20080152281, entitled "Substrates, systems and methods for analyzing materials", filed Oct. 31, 2007 by Lundquist et al., 20080152280, entitled "Substrates, systems and methods for analyzing materials", filed Oct. 31, 2007 by Lundquist et al., 20080145278, entitled "Uniform surfaces for hybrid material substrates and methods for making and using same", filed Oct. 31, 2007 by Korlach, 20080128627, entitled "SUBSTRATES, SYSTEMS AND METHODS FOR ANALYZING MATERIALS", filed Aug. 31, 2007 by Lundquist et al., 20080108082, entitled "Polymerase enzymes and reagents for enhanced nucleic acid sequencing", filed Oct. 22, 2007 by Rank et al., 20080095488, entitled "SUBSTRATES FOR PERFORMING ANALYTICAL REACTIONS", filed Jun. 11, 2007 by Foquet et al., 20080080059, entitled "MODULAR OPTICAL COMPONENTS AND SYSTEMS INCORPORATING SAME", filed Sep. 27, 2007 by Dixon et al., 20080050747, entitled "Articles having localized molecules disposed thereon and methods of producing and using same", filed Aug. 14, 2007 by Korlach et al., 20080032301, entitled "Articles having localized molecules disposed thereon and methods of producing same", filed Mar. 29, 2007 by Rank et al., 20080030628, entitled "Methods and systems for simultaneous real-time monitoring of optical signals from multiple sources", filed Feb. 9, 2007 by Lundquist et al., 20080009007, entitled "CONTROLLED INITIATION OF PRIMER EXTENSION", filed Jun. 15, 2007 by Lyle et al., 20070238679, entitled "Articles having localized molecules disposed thereon and methods of producing same", filed Mar. 30, 2006 by Rank et al., 20070231804, entitled "Methods, systems and compositions for monitoring enzyme activity and applications thereof", filed Mar. 31, 2006 by Korlach et al., 20070206187, entitled "Methods and systems for simultaneous real-time monitoring of optical signals from multiple sources", filed Feb. 9, 2007 by Lundquist et al., 20070196846, entitled "Polymerases for nucleotide analogue incorporation", filed Dec. 21, 2006 by Hanzel et al., 20070188750, entitled "Methods and systems for simultaneous real-time monitoring of optical signals from multiple sources", filed Jul. 7, 2006 by Lundquist et al., 20070161017, entitled "MITIGATION OF PHOTODAMAGE IN ANALYTICAL REACTIONS", filed Dec. 1, 2006 by Eid et al., 20070141598, entitled "Nucleotide Compositions and Uses Thereof", filed Nov. 3, 2006 by Turner et al., 20070134128, entitled "Uniform surfaces for hybrid material substrate and methods for making and using same", filed Nov. 27, 2006 by Korlach, 20070128133, entitled "Mitigation of photodamage in analytical reactions", filed Dec. 2, 2005 by Eid et al., 20070077564, entitled "Reactive surfaces, substrates and methods of producing same", filed Sep. 30, 2005 by Roitman et al., 20070072196, entitled "Fluorescent nucleotide analogs and uses therefore", filed Sep. 29, 2005 by Xu et al., and 20070036511, entitled "Methods and systems for monitoring multiple optical signals from a single source", filed Aug. 11, 2005 by Lundquist et al., and Korlach et al. (2008) "Selective aluminum passivation for targeted immobilization of single DNA polymerase molecules in zero-mode waveguide nanostructures" Proc. Natl. Acad. Sci. U.S.A. 105(4): 11761181—all of which are herein incorporated by reference in their entireties.

In some embodiments, nucleic acids are analyzed by determination of their mass and/or base composition. For example, in some embodiments, nucleic acids are detected and characterized by the identification of a unique base composition signature (BCS) using mass spectrometry (e.g., Abbott PLEX-ID system, Abbot Ibis Biosciences, Abbott Park, Ill.) described in U.S. Pat. Nos. 7,108,974, 8,017,743, and 8,017,322; each of which is herein incorporated by reference in its entirety.

In some embodiments, a MassARRAY system (Sequenom, San Diego, Calif.) is used to detect or analyze sequences (See e.g., U.S. Pat. Nos. 6,043,031; 5,777,324; and 5,605,798; each of which is herein incorporated by reference).

VI. Samples

The amplification methods, compositions, systems, and devices make use of samples which include a nucleic acid template. Samples may be derived from any suitable source, and for purposes related to any field, including but not limited to diagnostics, research, forensics, epidemiology, pathology, archaeology, etc. A sample may be biological, environmental, forensic, veterinary, clinical, etc. in origin. Samples may include nucleic acid derived from any suitable source, including eukaryotes, prokaryotes (e.g. infectious bacteria), mammals, humans, non-human primates, canines, felines, bovines, equines, porcines, mice, viruses, etc. Samples may contain, e.g., whole organisms, organs, tissues, cells, organelles (e.g., chloroplasts, mitochondria), synthetic nucleic acid, cell lysate, etc. Nucleic acid present in a sample (e.g. target nucleic acid, template nucleic acid, non-target nucleic acid, contaminant nucleic acid may be of any type, e.g., genomic DNA, RNA, microRNA, mitochondrial DNA, plasmids, bacteriophages, viruses, synthetic origin, natural origin, and/or artificial sequences (non-naturally occurring), synthetically-produced but naturally occurring sequences, etc. Biological specimens may, for example, include whole blood, lymphatic fluid, serum, plasma, sweat, tear, saliva, sputum, cerebrospinal (CSF) fluids, amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, aspirates (bone marrow, fine needle) and swabs or washes (e.g., oral, nasopharangeal, bronchial, bronchioalveolar, optic, rectal, intestinal, vaginal, epidermal, etc.) and/or other fresh, frozen, cultured, preserved (PAXgene™, RNAlater™, RNasin®, etc.) or archived biological specimens (formalin fixed paraffin-embedded (FFPE), fixed cell/lymphocyte pellet, etc.).

In some embodiments, samples are mixed samples (e.g. containing mixed nucleic acid populations). In some embodiments, samples analyzed by methods herein contain, or may contain, a plurality of different nucleic acid sequences. In some embodiments, a sample (e.g. mixed sample) contains one or more nucleic acid molecules (e.g. 1 ... 10 ... $10^2$ ... $10^3$ ... $10^4$ ... $10^5$ ... $10^6$ ... $10^7$, etc.) that contain a target sequence of interest in a particular application. In some embodiments, a sample (e.g. mixed sample) contains zero nucleic acid molecules that contain a target sequence of interest in a particular application. In some embodiments, a sample (e.g. mixed sample) contains nucleic acid molecules with a plurality of different sequences that all contain a target sequence of interest. In some embodiments, a sample (e.g. mixed sample) contains one or more nucleic acid molecules (e.g. 1 ... 10 ... $10^2$ ... $10^3$ ... $10^4$ ... $10^5$ ... $10^6$ ... $10^7$, etc.) that do not contain a target sequence of interest in a particular application. In some embodiments, a sample (e.g. mixed sample) contains zero nucleic acid molecules that do not contain a target sequence of interest in a particular application. In some embodiments, a sample (e.g. mixed sample) contains nucleic acid molecules with a plurality of different sequences that do not contain a target sequence of interest. In some embodiments, a sample contains more nucleic acid molecules that do not contain a target sequence than nucleic acid molecules that do contain a target sequence (e.g. 1.01:1 ... 2:1 ... 5:1 ... 10:1 ... 20:1 ... 50:1 ... $10^2$:1 ... $10^3$:1 ... $10^4$:1 ... $10^5$:1 ... $10^6$:1 ... $10^7$:1). In some embodiments, a sample contains more nucleic acid molecules that do contain a target sequence than nucleic acid molecules that do not contain a target sequence (e.g. 1.01:1 ... 2:1 ... 5:1 ... 10:1 ... 20:1 ... 50:1 ... $10^2$:1 ... $10^3$:1 ... $10^4$:1 ... $10^5$:1 ... $10^6$:1 ... $10^7$:1). In some embodiments, a sample contains a single target sequence that may be present in one or more nucleic acid molecules in the sample. In some embodiments, a sample contains two or more target sequences (e.g. 2, 3, 4, 5 ... 10 ... 20 ... 50 ... 100, etc.) that may each be present in one or more nucleic acid molecules in the sample.

In some embodiments, various sample processing steps may be accomplished to prepare the nucleic acid molecules within a sample, including, but not limited to cell lysis, restriction digestion, purification, precipitation, resuspension (e.g. in amplification buffer), dialysis, etc. In some embodiments, sample processing is performed before or after any of the steps including, but not limited to partitioning, amplification, re-amplification), amplicon detection, amplicon isolation, sequencing, etc.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claim.

We claim:

1. A method comprising:
   a) providing a device comprising:
      i) a microchannel comprising a surface configured for transmission a carrier medium comprising droplets,
      ii) a first thermal layer positioned along said microchannel configured to heat a portion of said microchannel surface to a nucleic acid denaturation temperature; and
      iii) a second thermal layer positioned along said microchannel configured to heat or cool a portion of said microchannel surface to a nucleic acid annealing temperature;
   wherein said first and said second thermal layers are positioned along opposing surface walls of said microchannel to create a thermal gradient across a cross-section of said microchannel, and wherein said thermal gradient comprises a nucleic acid denaturation zone, a nucleic acid annealing zone, and a nucleic acid polymerization zone; and
   b) flowing said carrier medium through said microchannel such that said droplets repeatedly pass through said thermal gradient causing temperature cycling in said droplets, wherein said droplets each comprise primers, a nucleic acid template, a polymerase, and nucleotides, and wherein said temperature cycling causes amplification of said nucleic acid templates in said droplets.

2. The method of claim 1, further comprising sequencing the amplified templates in at least some of the droplets.

3. The method of claim 2, wherein said sequencing comprises use of reversible dye terminators.

4. The method of claim 1, wherein flowing said carrier medium through said microchannel is performed in a continuous manner, a pulsed manner, a batch manner, or fed-batch manner.

5. The method of claim 1, wherein said device further comprises a plurality of motion components positioned along said microchannel, wherein said plurality of motion components are configured to impart motion to said droplets in said carrier medium when present in said microchannel such that stochastic contact of said droplet with said microchannel surface is increased.

6. The method of claim 5, wherein said motion is imparted via mechanical agitation.

7. The method of claim 6, wherein said mechanical agitation is selected from the group consisting of: vibration, low-frequency sonication, and acoustic waves.

8. The method of claim 5, wherein said motion is imparted via convection and/or turbulent flow.

9. The method of claim 5, wherein said motion is imparted via an electrical field.

10. The method of claim 5, wherein said droplets comprise paramagnetic microparticles, and wherein said plurality of motion components are configured to induce an oscillating magnetic field along said channel.

11. The method of claim 5, wherein said plurality of motion components are positioned intermittently along said microchannel.

12. The method of claim 1, further comprising monitoring template amplification with an optical array sensor positioned along said microchannel configured to monitor PCR signal output in said droplets.

13. The method of claim 1, wherein said optical array sensor comprises a component selected from the group consisting of: a light-emitting diode, a photodiode array, an optical fiber bundle, a laser configured for fluorometry, a piezoelectric crystal, an interdigital cantilever, a photovoltaic cell, and a gated linear CCD array.

14. The method of claim 1, wherein said droplets comprise an emulsion or a macromolecular assembly selected from the group consisting of: unilamellar vesicles, bilamellar vesicles, micelles, liposomes, nanostructures, macromolecular cages, carbon nanotubes, fullerenes or paramagnetic particles.

15. The method of claim 1, wherein said carrier medium is liquid carrier medium or a gas carrier medium.

16. The method of claim 1, wherein said droplets further comprise a detection reagent.

17. The method of claim 1, wherein said device further comprises a nucleic acid purification component.

\* \* \* \* \*